US008686156B2

(12) United States Patent
Füßlein et al.

(10) Patent No.: US 8,686,156 B2
(45) Date of Patent: Apr. 1, 2014

(54) THIAZOLE DERIVATIVES AS PESTICIDES

(75) Inventors: Martin Füßlein, Düsseldorf (DE); Thomas Bretschneider, Lohmar (DE); Reiner Fischer, Monheim (DE); Peter Jeschke, Bergisch Gladbach (DE); Adeline Köhler, Wuppertal (DE); Joachim Kluth, Langenfeld (DE); Friedrich August Mühlthau, Bad Soden am Taunus (DE); Arnd Voerste, Köln (DE); Yoshitaka Sato, Ibaraki (JP)

(73) Assignee: Bayer CropScience AG, Monheim (DE)

( * ) Notice: Subject to any disclaimer, the term of this patent is extended or adjusted under 35 U.S.C. 154(b) by 143 days.

(21) Appl. No.: 13/099,977

(22) Filed: May 3, 2011

(65) Prior Publication Data

US 2011/0319428 A1 Dec. 29, 2011

Related U.S. Application Data

(60) Provisional application No. 61/332,340, filed on May 7, 2010.

(30) Foreign Application Priority Data

May 5, 2010 (EP) .................................... 10162027

(51) Int. Cl.
| | | |
|---|---|---|
| C07D 401/04 | (2006.01) | |
| C07D 401/14 | (2006.01) | |
| C07D 403/04 | (2006.01) | |
| C07D 403/14 | (2006.01) | |
| A01N 43/40 | (2006.01) | |
| A01N 43/78 | (2006.01) | |
| A01N 43/66 | (2006.01) | |
| A01N 43/707 | (2006.01) | |

(52) U.S. Cl.
USPC ........ 546/269.7; 544/333; 544/334; 544/180; 514/256; 514/336; 546/268.1

(58) Field of Classification Search
USPC ......... 546/269.7; 544/333, 334; 514/256, 336
See application file for complete search history.

(56) References Cited

U.S. PATENT DOCUMENTS

| 4,528,291 | A | 7/1985 | Witkowski et al. |
|---|---|---|---|
| 6,231,786 | B1 | 5/2001 | Wingen et al. |
| 2002/0013326 | A1 | 1/2002 | Tiebes et al. |
| 2004/0116744 | A1 | 6/2004 | Furuya et al. |
| 2007/0066617 | A1 | 3/2007 | Mita et al. |
| 2007/0129407 | A1 | 6/2007 | Koyanagi et al. |
| 2008/0305955 | A1 | 12/2008 | Bretschneider et al. |
| 2009/0076282 | A1 | 3/2009 | Toriyabe et al. |
| 2009/0111847 | A1 | 4/2009 | Li et al. |
| 2009/0176779 | A1 | 7/2009 | Doerflinger et al. |
| 2009/0247551 | A1 | 10/2009 | Jeschke et al. |
| 2009/0253749 | A1 | 10/2009 | Jeschke et al. |
| 2009/0259046 | A1 | 10/2009 | Hamamoto et al. |
| 2010/0240705 | A1 | 9/2010 | Jeschke et al. |
| 2011/0306499 | A1 | 12/2011 | Bretschneider et al. |

FOREIGN PATENT DOCUMENTS

| CA | 2 671 179 A1 | 6/2008 |
|---|---|---|
| CA | 2 730 844 A1 | 1/2010 |
| DE | 197 25 450 A1 | 12/1998 |
| EP | 0 539 588 A1 | 5/1993 |
| JP | 2008-110953 | 5/2008 |
| JP | 2010-18586 | 1/2010 |
| WO | WO 03/015776 A1 | 2/2003 |
| WO | WO 03/106457 A1 | 12/2003 |
| WO | WO 2004/099160 A1 | 11/2004 |
| WO | WO 2005/035486 A1 | 4/2005 |
| WO | WO 2005/063094 A1 | 7/2005 |
| WO | WO 2006/056433 A2 | 6/2006 |
| WO | WO 2006/100288 A2 | 9/2006 |
| WO | WO 2007/047306 A1 | 4/2007 |
| WO | WO 2007/057407 A2 | 5/2007 |
| WO | WO 2007/075459 A2 | 7/2007 |
| WO | WO 2007/149134 A1 | 12/2007 |
| WO | WO 2008/104503 A1 | 9/2008 |
| WO | WO 2009/049851 A1 | 4/2009 |
| WO | WO 2010/005692 A2 | 1/2010 |
| WO | WO 2010/006713 A2 | 1/2010 |
| WO | WO 2010/074747 A1 | 7/2010 |
| WO | WO 2010/074751 A1 | 7/2010 |

OTHER PUBLICATIONS

Barnes, R.A. and Prochaska, R.J., "The Reaction of Bromine with Silver Salts of Aromatic Acids," *Journal of the American Chemical Society* 72:3188-3191, American Chemical Society, United States (1950).

Begtrup, M. and Hansen, L.B.L., "New Methods for the Introduction of Substituents into Thiazoles," *Acta Chemica Scandinavica* 46:372-383, Munksgaard International Publishers, Denmark (1992).

Friedmann, A., et al., "Substitution électrophile en série thiazolique (Note de Laboratoire)," *Bulletin de la Société Chimique de France* 8-9:3155-3157, Société Chimique de France, France (1970).

Giraud, M., et al., "Synthesis and photochromism of two new 1,2-bis(thiazolyl) perfluorocyclopentenes with chelating sites," *New J. Chem.* 29:439-446, The Royal Society of Chemistry and the Centre National de la Recherche Scientifique, France (2005).

Hodgetts, K.J. and Kershaw, M.T., "Regiocontrolled Synthesis of Substituted Thiazoles," *Org. Lett.* 4(8):1363-1365, American Chemical Society, United States (2002).

Nakagawa, H., et al., "Synthesis and Photochemical Reactions of Photochromic Terarylene Having a Leaving Methoxy Group," *Org. Lett.* 11(7):1475-1478, American Chemical Society, United States (2009).

Yamanaka, H., et al., "On The Reactivity of Halo-1,3-Azoles and Related Compounds Toward Aromatic $S_N2$ Substitution," *Heterocycles* 31(6):1115-1127, Sendai Institute of Heterocyclic Chemistry, Japan (1990).

International Search Report for International Application No. PCT/EP2011/056973, European Patent Office, Netherlands, mailed Aug. 17, 2011.

English language Abstract of Japanese Patent Publication No. 2008-110953, published May 15, 2008, Japanese Patent Office, Patent Abstracts of Japan.

English language Abstract of Japanese Patent Publication No. 2010-018586, published Jan. 28, 2010, Japanese Patent Office, Patent Abstracts of Japan.

*Primary Examiner* — Venkataraman Balasubramanian

(74) *Attorney, Agent, or Firm* — Sterne, Kessler, Goldstein & Fox P.L.L.C.

(57) ABSTRACT

The present application relates to novel heterocyclic compounds, to their use for controlling animal pests including arthropods and in particular insects, and to processes for preparing the novel compounds.

13 Claims, No Drawings

THIAZOLE DERIVATIVES AS PESTICIDES

The present application relates to novel heterocyclic compounds, to compositions comprising these compounds, to their use for controlling animal pests including arthropods and in particular insects, and to processes for preparing the novel compounds.

Certain thiazolyl compounds are already known; however, their use for controlling animal pests has hitherto not been described (cf. WO 2003/015776 A1).

Recently, further thiazolyl compounds suitable for use in crop protection have been disclosed (WO 2010/006713 A1).

Modern crop protection agents have to satisfy many demands, for example with respect to efficacy, persistence and spectrum of their action and possible use. Questions of toxicity, the combinability with other active compounds or formulation auxiliaries play a role, as well as the question of the expense that the synthesis of an active compound requires. Furthermore, resistances may occur. For all these reasons, the search for novel crop protection agents cannot be considered as having been concluded, and there is a constant need for novel compounds having properties which, compared to the known compounds, are improved at least in respect of individual aspects.

It was an object of the present invention to provide compounds which widen the spectrum of the pesticides under various aspects.

This object and further objects not explicitly mentioned which can be derived or deduced from the context discussed here are achieved by novel compounds of the formula (I)

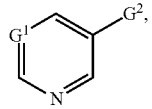

(I)

in which
G$^1$ represents N, CH or C-halogen,
G$^2$ represents

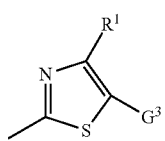

(A)

in which
R$^1$ represents cyano, nitro or halogen and
G$^3$ represents a substituted heterocycle from the group consisting of dioxanyl, oxazolinyl, dihydrooxadiazinyl, dihydrodioxazinyl and hydroxypyridyl, or
G$^3$ represents heteroaryl which is substituted by optionally substituted heterocyclyl from the group consisting of triazolinonyl, dihydrodioxazinyl, dihydrooxadiazinyl, dioxolanyl, dioxanyl (in particular 1,3-dioxan-2-yl), piperidinonyl, pyrrolidinonyl and pyrazolinonyl, by optionally substituted phenyl, by optionally substituted heteroaryl or by optionally substituted heteroarylalkyl,
and also salts, metal complexes and N-oxides of the compounds of the formula (I).

It has been found that compounds of the formula (I) have pronounced biological properties and are suitable especially for controlling animal pests, in particular insects, arachnids and nematodes, encountered in agriculture, in forests, in the protection of stored products and materials and in the hygiene sector.

Preferred substituents or ranges of the radicals mentioned in the compounds of the formula (I) shown above are illustrated below.

Preference is given to compounds of the formula (I)

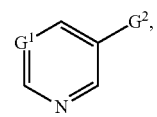

(I)

in which the substituents have the following meanings:
G$^1$ represents N, CH or C-halogen.
G$^2$ represents

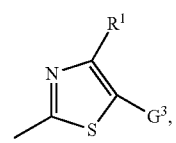

(A)

in which
R$^1$ represents a radical from the group consisting of cyano, nitro, fluorine, chlorine, bromine and iodine.
G$^3$ represents a heterocycle from the group consisting of dioxanyl, oxazolinyl, dihydrooxadiazinyl, dihydrodioxazinyl and hydroxypyridyl which is substituted by one or more radicals from the group consisting of halogen, cyano, nitro, alkyl, haloalkyl, cycloalkyl, alkoxy, haloalkoxy, alkylthio, haloalkylthio, alkylsulphinyl, alkylsulphonyl, alkylsulphinyl, haloalkylsulphonyl, amino, alkylamino, dialkylamino, alkylcarbonylamino, alkoxycarbonylamino, alkoxyalkyl, haloalkoxyalkyl, alkenyl, alkynyl, cycloalkylalkyl, alkylcarbonyl, alkoxycarbonyl, aminocarbonyl, pyridyl and pyrimidyl
G$^3$ also represents heteroaryl from the group consisting of pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl, in particular pyridyl, pyrimidyl, imidazolyl, pyrazolyl, triazinyl, thiazolyl, thiadiazolyl, oxadiazolyl and oxazolyl which is substituted by a heterocyclyl radical from the group consisting of triazolinonyl, dihydrodioxazinyl, dihydrooxadiazinyl, dioxolanyl, dioxanyl (in particular 1,3-dioxan-2-yl), piperidinonyl, pyrrolidinonyl and pyrazolinonyl (which for its part may be substituted by alkyl and haloalkyl), by phenyl (which for its part may be substituted by halogen, cyano, nitro, alkyl and haloalkyl), by a heteroaryl radical from the group consisting of pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for its part may be substituted by halogen, nitro, alkyl, haloalkyl, alkoxy, haloalkoxy, alkoxyalkyl, alkylthio, alkylthioalkyl and cycloalkyl) or by a heteroarylalkyl radical from the group consisting of triazolylalkyl, pyridylalkyl, pyrimidylalkyl and oxadiazolylalkyl (which for its part may be substituted by alkyl).

Particular preference is given to compounds of the formula (I)

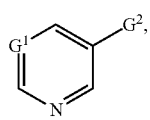

(I)

in which the substituents have the following meanings:
$G^1$ represents N, CH or C-halogen (in the case of C-halogen in particular C—F, C—Cl or C—Br).
$G^2$ represents

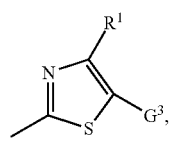

(A)

in which
$R^1$ represents cyano, fluorine or chlorine.
$G^3$ represents a heterocycle from the group consisting of 1,3-dioxan-2-yl, oxazolinyl, dihydrooxadiazinyl, dihydrodioxazinyl and hydroxypyridyl which is substituted by one or more radicals from the group consisting of halogen, cyano, nitro, $C_1$-$C_6$-alkyl, $C_1$-$C_6$-haloalkyl, $C_3$-$C_6$-cycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-alkylsulphonyl, $C_1$-$C_6$-haloalkylsulphinyl, $C_1$-$C_6$-haloalkylsulphonyl, amino, $C_1$-$C_6$-alkylamino, di-($C_1$-$C_6$-alkyl)amino, $C_1$-$C_6$-alkylcarbonylamino, $C_1$-$C_6$-alkoxycarbonylamino, $C_1$-$C_6$-alkoxy-$C_1$-$C_6$-alkyl, $C_2$-$C_6$-alkenyl, $C_2$-$C_6$-alkynyl, $C_3$-$C_6$-cycloalkyl-$C_1$-$C_6$-alkyl, $C_1$-$C_6$-alkylcarbonyl, $C_1$-$C_6$-alkoxycarbonyl, aminocarbonyl, pyridyl and pyrimidyl.
$G^3$ also represents heteroaryl from the group consisting of pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl (in particular pyridyl, pyrimidyl, imidazolyl, pyrazolyl, triazinyl, thiazolyl, thiadiazolyl, oxadiazolyl and oxazolyl), each of which is substituted by a heterocyclyl radical from the group consisting of morpholinyl, triazolinonyl, dihydrodioxazinyl, dihydrooxadiazinyl, dioxolanyl, dioxanyl piperidinonyl, pyrrolidinonyl and pyrazolinonyl (which for its part may be substituted by $C_1$-$C_6$-alkyl and $C_1$-$C_6$-haloalkyl), by phenyl (which for its part may be substituted by halogen, cyano, nitro, $C_1$-$C_6$-alkyl and $C_1$-$C_6$-haloalkyl), by a heteroaryl radical from the group consisting of pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for its part may be substituted by halogen, nitro, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, $C_1$-$C_6$-alkylthio-$C_1$-$C_6$-alkyl and $C_3$-$C_6$-cycloalkyl) or by a heteroarylalkyl radical from the group consisting of triazolyl-$C_1$-$C_6$-alkyl, pyridyl-$C_1$-$C_6$-alkyl, pyrimidyl-$C_1$-$C_6$-alkyl and oxadiazolyl-$C_1$-$C_6$-alkyl (which for its part may be substituted by $C_1$-$C_6$-alkyl).

Very particular preference is given to compounds of the formula (I)

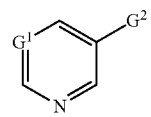

(I)

in which the substituents have the following meanings:
$G^1$ represents N, CH or C-halogen (in the case of C-halogen in particular C—F or C—Cl).
$G^2$ represents

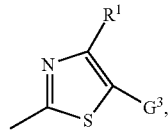

(A)

in which
$R^1$ represents cyano, fluorine or chlorine.
$G^3$ represents a heterocycle from the group consisting of 1,3-dioxan-2-yl, oxazolinyl, dihydrooxadiazinyl, dihydrodioxazinyl and hydroxypyridyl which is substituted by one or more radicals from the group consisting of halogen, cyano, nitro, $C_1$-$C_4$-alkyl, $C_1$-$C_4$-haloalkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulphinyl, $C_1$-$C_4$-alkylsulphonyl, $C_1$-$C_4$-haloalkylsulphinyl, $C_1$-$C_4$-haloalkylsulphonyl, amino, $C_1$-$C_4$-alkylamino, di-($C_1$-$C_4$-alkyl)amino, $C_1$-$C_4$-alkylcarbonylamino, $C_1$-$C_4$-alkoxycarbonylamino, $C_1$-$C_4$-alkoxy-$C_1$-$C_4$-alkyl, $C_1$-$C_4$-haloalkoxy-$C_1$-$C_4$-alkyl, $C_2$-$C_4$-alkenyl, $C_2$-$C_4$-alkynyl, $C_3$-$C_6$-cycloalkyl-$C_1$-$C_4$-alkyl, $C_1$-$C_4$-alkylcarbonyl, $C_1$-$C_4$-alkoxycarbonyl, aminocarbonyl, pyridyl and pyrimidyl.
$G^3$ also represents a heteroaryl radical from the group consisting of pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl (in particular pyridyl, pyrimidyl, imidazolyl, pyrazolyl, triazinyl, thiazolyl, thiadiazolyl, oxadiazolyl and oxazolyl) which is substituted by a heterocyclyl radical from the group consisting of morpholinyl, triazolinonyl, dihydrodioxazinyl, dihydrooxadiazinyl, dioxolanyl, dioxanyl, piperidinonyl, pyrrolidinonyl and pyrazolinonyl (which for its part may be substituted by $C_1$-$C_4$-alkyl and $C_1$-$C_4$-haloalkyl), by phenyl (which for its part may be substituted by halogen, cyano, nitro, $C_1$-$C_4$-alkyl and $C_1$-$C_4$-haloalkyl), by a heteroaryl radical from the group consisting of pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for its part may be substituted by halogen, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkoxy-$C_1$-$C_4$-alkyl, $C_1$-$C_4$-alkylthio, $C_1$-$C_4$-alkylthio-$C_1$-$C_4$-alkyl and $C_3$-$C_6$-cycloalkyl) or by a heteroarylalkyl radical from the group consisting of triazolyl-$C_1$-$C_4$-alkyl, pyridyl-$C_1$-$C_4$-alkyl, pyrimidyl-$C_1$-$C_4$-alkyl and oxadiazolyl-$C_1$-$C_4$-alkyl (which for its part may be substituted by $C_1$-$C_4$-alkyl).

Very particular emphasis is given to compounds of the formula (I)

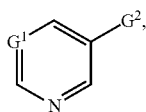

(I)

in which the substituents have the following meanings:
$G^1$ represents N, CH or C-halogen (in the case of C-halogen in particular C—F).
$G^2$ represents

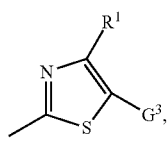

(A)

in which
$R^1$ represents fluorine or chlorine.
$G^3$ represents in each case optionally pyridyl- or pyrimidinyl-substituted 1,3-dioxan-2-yl, oxazolinyl, dihydrooxadiazinyl or hydroxypyridyl,
$G^3$ also represents a heteroaryl radical from the group consisting of pyrazolyl, 1,2,4-oxadiazolyl, pyridyl, pyrimidinyl, 1,3,5-triazinyl, triazinyl and oxadiazolyl which is substituted by a heterocyclyl radical from the group consisting of morpholinyl, triazolinonyl, dihydrodioxazinyl, dihydrooxadiazinyl, piperidinonyl, pyrrolidinonyl and pyrazolinonyl (which for its part may be substituted by $C_1$-$C_4$-alkyl (in particular methyl) and $C_1$-$C_4$-haloalkyl (in particular $CF_3$)), by phenyl (which for its part may be substituted by halogen (in particular fluorine, chlorine)), by a heteroaryl radical from the group consisting of pyrrolyl, pyridyl (in particular 2-pyridyl), pyridyl N-oxide, pyrimidinyl (in particular 2-pyrimidinyl), pyrazolyl (in particular 1-pyrazolyl and 3-pyrazolyl), thiazolyl, furanyl, thienyl, triazolyl, oxadiazolyl, thiadiazolyl (in particular 1,2,4-thiadiazol-3-yl), pyrazinyl, triazinyl and isoquinolinyl (which for its part may be substituted by halogen (in particular fluorine, chlorine), nitro, $C_1$-$C_4$-alkyl (in particular methyl, ethyl, n-propyl, isopropyl, tert-butyl), $C_1$-$C_4$-haloalkyl (in particular $CF_3$, $CHF_2$, $CFClH$), $C_1$-$C_4$-alkoxy (in particular methoxy, ethoxy), $C_3$-$C_6$-cycloalkyl (in particular cyclopropyl, cyclobutyl, cyclopentyl)) or by a heteroarylalkyl radical from the group consisting of triazolyl-$C_1$-$C_4$-alkyl (in particular triazolylmethyl), pyridyl-$C_1$-$C_4$-alkyl (in particular pyridylmethyl), pyrimidinyl-$C_1$-$C_4$-alkyl (in particular pyrimidinylmethyl) and oxadiazolyl-$C_1$-$C_4$-alkyl (in particular oxadiazolylmethyl (which for its part may be substituted by $C_1$-$C_4$-alkyl (in particular methyl)).

Halogen-substituted radicals, for example haloalkyl, are mono- or polyhalogenated, up to the maximum number of possible substituents. In the case of polyhalogenation, the halogen atoms can be identical or different. Here, halogen denotes fluorine, chlorine, bromine and iodine, in particular fluorine, chlorine and bromine, especially fluorine and chlorine.

The radical "pyrimidyl" is also referred to as "pyrimidinyl".

Saturated or unsaturated hydrocarbon radicals, such as alkyl or alkenyl, can in each case be straight-chain or branched as far as this is possible, including in combination with heteroatoms, such as, for example, in alkoxy.

Optionally substituted radicals can be mono- or polysubstituted, where in the case of polysubstitution the substituents can be identical or different.

The general or preferred radical definitions or illustrations given above apply both to the end products and, correspondingly, to the starting materials and intermediates. These radical definitions can be combined with one another as desired, i.e. including combinations between the given preferred ranges.

Preference according to the invention is given to compounds of the formula (I) which contain a combination of the meanings listed above as being preferred.

Particular preference according to the invention is given to compounds of the formula (I) which contain a combination of the meanings listed above as being particularly preferred.

Very particular preference according to the invention is given to compounds of the formula (I) which contain a combination of the meanings listed above as being very particularly preferred.

Very particular emphasis according to the invention is given to compounds of the formula (I) which contain a combination of the meanings listed above as being very especially preferred.

In a special group of compounds of the formula (I) according to the invention, $G^1$ represents CH.

In a further special group of compounds of the formula (I) according to the invention, $G^1$ represents N.

In a further special group of compounds of the formula (I) according to the invention, $G^1$ represents C-halogen.

In a further special group of compounds of the formula (I) according to the invention, $G^3$ represents a heterocycle.

In a further special group of compounds of the formula (I) according to the invention, $G^3$ represents heteroaryl.

In a further special group of compounds of the formula (I) according to the invention, $G^1$ represents CH and represents fluorine.

In a further special group of compounds of the formula (I) according to the invention, $G^1$ represents N and $R^1$ represents fluorine.

In a further special group of compounds of the formula (I) according to the invention, $G^1$ represents C-halogen and $R^1$ represents fluorine.

In a further special group of compounds of the formula (I) according to the invention, $G^1$ represents CH and $R^1$ represents chlorine.

In a further special group of compounds of the formula (I) according to the invention, $G^1$ represents N and $R^1$ represents chlorine.

In a further special group of compounds of the formula (I) according to the invention, $G^1$ represents C-halogen and $R^1$ represents chlorine.

In a further special group of compounds of the formula (I) according to the invention, $G^1$ represents CH and $R^1$ represents cyano.

In a further special group of compounds of the formula (I) according to the invention, $G^1$ represents N and $R^1$ represents cyano.

In a further special group of compounds of the formula (I) according to the invention, $G^1$ represents C-halogen and $R^1$ represents cyano.

The compounds of the formula (I) may, where appropriate, depending on the nature of the substituents, be in the form of geometric and/or optically active isomers or corresponding isomer mixtures of varying composition. The invention relates both to the pure isomers and to the isomer mixtures.

By way of example and additionally, the preparation of compounds of the formula (I) is illustrated in the formula scheme below. Reference may also be made here to the Preparation Examples,

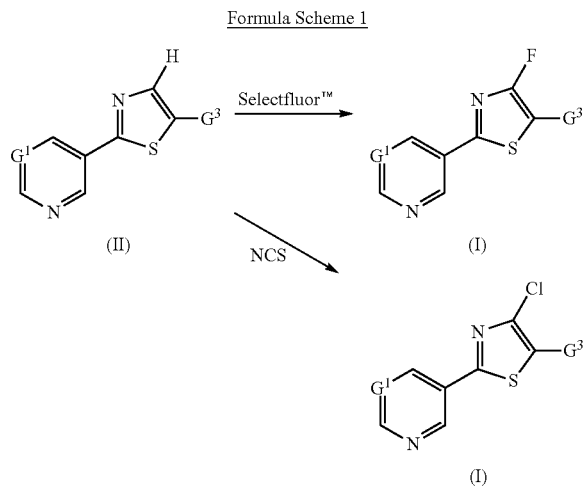

Formula Scheme 1

Compounds of type (II) can be obtained as described in WO 2010/006713.

In accordance with Formula Scheme 1, they are converted by reaction with a fluorinating agent such as 1-(chloromethyl)-4-fluoro-1,4-diazoniabicyclo[2.2.2]octane ditetrafluoroborate (Selectfluor™) in a diluent such as acetonitrile into the compounds of the formula (I) according to the invention where $R^1$=F or by reaction with a chlorinating agent such as N-chlorosuccinimide (NCS) into the compounds of the formula (I) according to the invention where $R^1$=Cl.

A fluorination of this type is described, for example, in U.S. Pat. No. 6,231,786.

A chlorination of this type is described, for example, in Heterocycles, 199, vol. 31, No. 6, 1115-1127.

A bromination of this type is described, for example, in Acta Chem. Scand. 1992, 46, 372-383. Alternatively, the bromine compound can be prepared by regioselective palladium-catalyzed coupling of the 4,5-dibromothiarole with boronic acid or corresponding organometallic compounds (Org. Lett. 2009, 11, 1475-1478).

4-Cyanothiazoles have also been described in the literature, see, for example, U.S. Pat. No. 4,528,291, WO 2007/47306, US 2009/176779.

4-Nitrothiazoles have been described, too, see, for example, Journal of the American Chemical Society, 1950, vol. 72, 3188 and Bulletin de la Société Chimique de France, 1970, 3155-3157.

4-Bromothiazoles have also been described, see, for example, Heterocycles, 199, vol. 31, No. 6, 1115-1127, Organic Letters 2002, vol. 4, No. 8, 1363-1366 and New Journal of Chemistry, 2005, vol. 29, No. 3, 439-446.

The active compounds according to the invention, in combination with good plant tolerance, favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as crop protection agents. They are active against normally sensitive and resistant species and also against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulca-* tus, *Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus*.

From the order of the Dermaptera, for example, *Forficula auricularia*.

From the order of the Diplopoda, for example, *Blaniulus guttulatus*,

From the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti*.

It is furthermore possible to control protozoa, such as *Eimeria*.

From the order of the Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.

From the order of the Homoptera, for example, *Acyrthosipon* spp., *Aeneolamia* spp., *Agonoscena* spp., *Aleut odes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii*.

From the order of the Hymenoptera, for example, *Diprion* spp., *Hoplocampa* spp., *Lasius* spp., *Monomorium pharaonic* and *Vespa* spp.

From the order of the Isopoda, for example, *Armadillidium vulgare, Oniscus asellus* and *Porcellio scaber*.

From the order of the Isoptera, for example, *Reticulitermes* spp. and *Odontotermes* spp.

From the order of the Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Chematobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.

From the order of the Orthoptera, for example, *Acheta domesticus, Blatta orientalis, Blattella gemanica, Gryllotalpa* spp., *Leucophaea maderae, Locusta* spp., *Melanoplus* spp., *Periplaneta americana, Schistocerca gregaria*.

From the order of the Siphonaptera, for example, *Ceratophyllus* spp. and *Xenopsylla cheopis*.

From the order of the Symphyla, for example, *Scutigerella immaculata*.

From the order of the Thysanoptera, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni* and *Thrips* spp.

From the order of the Thysanura, for example, *Lepisma saccharina*.

The phytoparasitic nematodes include, for example, *Anguina* spp., *Aphelenchoides* spp., *Belonoaimus* spp., *Bur-*

*saphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans* and *Xiphinema* spp.

The compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (mycoplasma-like organisms) and RLO (rickettsia-like organisms). They can also be used as intermediates or precursors for the synthesis of other active compounds.

The active compounds can be converted into the customary formulations, such as solutions, emulsions, wettable powders, water- and oil-based suspensions, powders, dusts, pastes, soluble powders, soluble granules, granules for broadcasting, suspoemulsion concentrates, natural compounds impregnated with active compound, synthetic substances impregnated with active compound, fertilizers and also microencapsulations in polymeric substances.

These formulations are produced in a known manner, for example by mixing the active compounds with extenders, that is, liquid solvents and/or solid carriers, optionally with the use of surfactants, that is to say emulsifiers and/or dispersants and/or foam-formers. The formulations are prepared either in suitable facilities or else before or during application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

Suitable solid carriers are:

for example ammonium salts and ground natural minerals such as kaolins, clays, talc, chalk, quartz, attapulgite, montmorillonite or diatomaceous earth, and ground synthetic materials such as highly disperse silica, alumina and silicates; suitable solid carriers for granules are: for example, crushed and fractionated natural rocks such as calcite, marble, pumice, sepiolite and dolomite, and also synthetic granules of inorganic and organic meals, and also granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulfonates, alkyl sulphates, arylsulfonates and also protein hydrolysates; suitable dispersants are nonionic and/or ionic substances, for example from the classes of the alcohol-POE and/or -POP ethers, acid and/or POP/POE esters, alkylaryl and/or POP/POE ethers, fat and/or POP/POE adducts, POE- and/or POP-polyol derivatives, POE- and/or POP-sorbitan or -sugar adducts, alkyl or aryl sulphates, alkyl- or arylsulphonates and alkyl or aryl phosphates or the corresponding PO-ether adducts. Furthermore, suitable oligomers or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and also their adducts with formaldehyde.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

Other possible additives are perfumes, mineral or vegetable oils which are optionally modified, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability, may also be present.

The formulations generally comprise between 0.01 and 98% by weight of active compound, preferably between 0.5 and 90%.

The active compounds according to the invention may be used as they are or in their formulations, including in a mixture with one or more suitable fungicides, bactericides, acaricides, nematicides, insecticides, microbicides, fertilizers, attractants, sterilants, synergists, safeners, semiochemicals and/or plant growth regulators, in order thereby, for example, to broaden the activity spectrum, to prolong the duration of action, to increase the rate of action, to prevent repulsion or to prevent development of resistance. Furthermore, active compound combinations of this kind may improve plant growth, raise tolerance towards high or low temperatures, against drought or against increased levels of water and/or soil salt, improve flowering performance, facilitate harvesting and increase yields, accelerate ripening, increase the quality and/or nutritional value of the harvested products, prolong storage life and/or improve the manageability of the harvested products. Combining the active compounds of the invention and co-components generally produces synergistic effects—that is, the activity of the mixture in question is greater than the activity of the individual components. In general it is possible to use the combinations not only in premixes, tank mixes or ready-made mixes but also as seed applications.

Particularly favourable co-components in mixtures are, for example, the following compounds:

Insecticides/acaricides/nematicides:

The active compounds identified here by their common name are known and are described, for example, in the pesticide handbook ("The Pesticide Manual" 14th Ed., British Crop Protection Council 2006) or can be found on the Internet (e.g. http://www.alanwood.net/pesticides).

(1) Acetylcholinesterase (AChE) inhibitors, such as, for example, carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos-ethyl, azinphos-methyl, cadusafos, chlorethoxyfos, chlorfenvinphos, chlormephos, chlorpyrifos, chlorpyriphos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel antagonists, such as, for example, cyclodiene organochlorines, for example chlordane and endosulfan; or phenylpyrazoles (fiproles), for example ethiprole and fipronil.

(3) Sodium channel modulators/voltage-gated sodium channel blockers, such as, for example, pyrethroids, for example acrinathrin, allethrin, d-cis-trans-allethrin, d-trans-allethrin, bifenthrin, bioallethrin, bioallethrin-S-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans-isomers], deltamethrin, empenthrin [(EZ)-(1R)-isomers], esfenvalerate, etofenprox, fenpropathrin, fenvalerate, flucythrinate, flumethrin, tau-fluvalinate, haltenprox, imiprothrin, kadethrin, permethrin, phenothrin [(1R)-trans-isomer], prallethrin, pyrethrins (pyrethrum), resmethrin, silafluofen, tefluthrin, tetramethrin, tetramethrin [(1R)-isomers], tralomethrin and transfluthrin; or DDT; or methoxychlor.

(4) Nicotinergic acetylcholine receptor (nAChR) agonists, such as, for example, neonicotinoids, for example acetamiprid, clothianidin, dinotefuran, itridacloprid, nitenpyram, thiacloprid and thiamethoxam; or nicotine.

(5) Allosteric nicotinergic acetylcholine receptor (nAChR) activators, such as, for example, spinosyns, for example spinetoram and spinosad.

(6) Chloride channel activators, for example avermectins/milbemycins, for example abamectin, emamectin benzoate, lepimectin and milbemectin.

(7) Juvenile hormone mimics, such as, for example, juvenile hormone analogues, for example hydroprene, kinoprene and rnethoprene; or fenoxycarb; or pyriproxyfen.

(8) Active compounds having an unknown or unspecific mechanism of action, such as, for example, fumigants, for example methyl bromide and other alkyl halides; or chloropicrin; or sulphuryl fluoride; or borax; or tartar emetic.

(9) Selective antifeedants, for example pymetrozine; or flonicamid.

(10) Mite growth inhibitors, for example clofentezine, hexythiazox and diflovidazin; or etoxazole.

(11) Microbial disruptors of the insect gut membrane, for example *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis*, and BT plant proteins: Cry1Ab, Cry1Ac, Cry1Fa, Cry2Ab, mCry3A, Cry3Ab, Cry3Bb, Cry34/35Ab1.

(12) Oxidative phosphorylation inhibitors, ATP disruptors, such as, for example, diafenthiuron; or organotin compounds, for example azocyclotin, cyhexatin and fenbutatin oxide; or propargite; or tetradifon.

(13) Oxidative phosphorylation decouplers acting by interrupting the H proton gradient, such as, for example, chlorfenapyr, DNOC and Sulfluramid.

(14) Nicotinergic acetylcholine receptor antagonists, such as, for example, bensultap, cartap hydrochloride, thiocylam, and thiosultap-sodium.

(15) chitin biosynthesis inhibitors, type 0, such as, for example, bistrifluoron, chlorfluazuron, diflubenzuron, flucycloxui on, flufenoxuron, hexaflumuron, lufenuron, novaluron, noviflumuron, teflubenzuron and triflumuron.

(16) Chitin biosynthesis inhibitors, type 1, such as, for example, buprofezin.

(17) Moulting disruptors, such as, for example, cyromazine.

(18) Ecdysone receptor agonists, such as, for example, chromafenozide, halofenozide, methoxyfenozide and tebufenozide.

(19) Octopaminergic agonists, such as, for example, amitraz.

(20) Complex-III electron transport inhibitors, such as, for example, hydramethylnone; or acequinocyl; or fluacrypyrim;

(21) Complex-I electron transport inhibitors, for example

METI acaricides, for example fenazaquin, fenpyroximate, pyrimidifen, pyridaben, tebufenpyrad and tolfenpyrad; or rotenone (Derris).

(22) Voltage-gated sodium channel blockers, for example indoxacarb; or metaflumizone.

(23) Inhibitors of acetyl-CoA carboxylase, such as, for example, tetronic and tetramic acid derivatives, for example spirodiclofen, spiromesifen and spirotetramat.

(24) Complex-IV electron transport inhibitors, such as, for example, phosphines, for example aluminium phosphide, calcium phosphide, phosphine, zinc phosphide; or cyanide.

(25) Complex-II electron transport inhibitors, such as, for example, cyenopyrafen.

(28) Ryanodine receptor effectors, such as, for example,

Diamides, for example chlorantraniliprole and flubendiamide.

Further active compounds with an unknown mechanism of action, such as, for example, amidoflumet, azadiraatin, benclothiaz, benzoximate, bifenazate, bromopropylate, chinomethionat, cryolite, cyflumetofen (Cyazypyr), cyflumetofen, dicofol, diflovidazin, fluensulfone, flufenerim, flufiprole, fluopyram, flufenozide, imidaclothiz, iprodione, pyridalyl, pyrifluquinazon and iodomethane; furthermore products based on *Bacillus firmus* (I-1582, BioNeem, Votivo) and also the known active compounds below:

3-bromo-N-{2-bromo-4-chloro-6-[(1-cyclopropylethyl)carbamoyl]phenyl}-1-(3-chloropyridin-2-yl)-1H-pyrazole-5-carboxamide (known from WO2005/077934), 4-{[(6-bromopyrid-3-yl)methyl](2-fluoroethyl)amino}furan-2(5H)-one (known from WO2007/115644), 4-{[(6-fluoropyrid-3-yl)methyl](2,2-difluoroethyl)amino}furan-2(5H)-one (known from WO2007/115644), 4-{[(2-chloro-1,3-thiazol-5-yl)methyl](2-fluoroethyl)amino}furan-2(5H)-one (known from WO2007/115644), 4-{[(6-chloropyrid-3-yl)methyl](2-fluoroethyl)amino}furan-2(5H)-one (known from WO2007/115644), 4-{[(6-chloropyrid-3-yl)methyl](2,2-difluoroethyl)amino}furan-2(5H)-one (known from WO2007/115644), 4-{[(6-chloro-5-fluoropyrid-3-yl)methyl](methyl)amino}furan-2(5H)-one (known from WO2007/115643), 4-{[(5,6-dichloropyrid-3-yl)methyl](2-fluoroethyl)amino}furan-2(5H)-one (known from WO2007/115646), 4-{[(6-chloro-5-fluoropyrid-3-yl)methyl](cyclopropyl)amino}furan-2(5H)-one (known from WO2007/115643), 4-{[(6-chloropyrid-3-yl)methyl](cyclopropyl)amino}furan-2(5H)-one (known from EP-A-0 539 588), 4-{[(6-chloropyrid-3-yl)methyl](methyl)amino}furan-2(5H)-one (known from EP-A-0 539 588), {[1-(6-chloropyridin-3-yl)ethyl](methyl)oxido-λ$^4$-sulphanylidene}cyanamide (known from WO2007/149134) and its diastereomers {[(1R)-1-(6-chloropyridin-3-yl)ethyl](methyl)oxido-λ$^4$-sulphanylidene}cyanamide (A) and {[(1S)-1-(6-chloropyridin-3-yl)ethyl](methyl)oxido-λ$^4$-sulphanylidene}cyanamide (B) (likewise known from WO2007/149134) and sulfoxaflor (likewise known from WO2007/149134) and its diastereomers [(R)-methyl(oxido){(1R)-1-[6-(trifluoromethyl)pyridin-3-yl]ethyl}-λ$^4$-sulphanylidene]cyanamide (A1) and [(S)-methyl(oxido){(1S)-1-[6-(trifluoromethyl)pyridin-3-yl]ethyl}-λ$^4$-sulphanylidene]cyanamide (A2), referred to as diastereomer group A (known from WO 2010/074747, WO 2010/074751), [(R)-methyl(oxido){(1S)-1-[6-(trifluoromethyl)pyridin-3-yl]ethyl}-λ$^4$-sulphanylidene]cyanamide (B1) and [(S)-methyl(oxido){(1R)-1-[6-(trifluoromethyl)pyridin-3-yl]ethyl}-λ$^4$-sulphanylidene]cyanamide (B2), referred to as diastereomer group B (likewise known from WO 2010/074747, WO 2010/074751) and 11-(4-chloro-2,6-dimethylphenyl)-12-hydroxy-1,4-dioxa-9-azadispiro[4.2.4.2]tetradec-11-en-10-one (known from WO2006/089633), 3-(4'-fluoro-2,4-dimethylbiphenyl-3-yl)-4-hydroxy-8-oxa-1-azaspiro[4.5]dec-3-en-2-one (known from WO2008/067911), 1-{2-fluoro-4-methyl-5-[(2,2,2-trifluoroethyl)sulphinyl]phenyl}-3-(trifluoromethyl)-1H-1,2,4-triazole-5-amine (known from WO2006/043635), [(3S,4aR,12R,12aS,12bS)-3-[(cyclopropylcarbonyl)oxy]-6,12-dihydroxy-4,12b-dimethyl-11-oxo-9-(pyridin-3-yl)-1,3,4,4a,5,6,6a,12,12a,12b-decahydro-2H,11H-benzo[f]pyrano[4,3-b]chromen-4-yl]methylcyclopropane carboxylate (known from WO2008/066153), 2-cyano-3-(difluoromethoxy)-N,N-dimethylbenzenesulphonamide (known from WO2006/056433), 2-cyano-3-(difluoromethoxy)-N-methylbenzenesulphonamide (known from WO2006/100288), 2-cyano-3-(difluoromethoxy)-N-ethylbenzenesulphonamide (known from WO2005/035486), 4-(difluoromethoxy)-N-ethyl-N-methyl-1,2-benzothiazole-3-amine 1,1-dioxide (known from WO2007/057407), N-[1-(2,3-dimethylphenyl)-2-(3,5-dimethylphenyl)ethyl]-4,5-dihydro-1,3-thiazole-2-amine (known from WO2008/104503), {1'-[(2E)-3-(4-chlorophenyl)prop-2-en-1-yl]-5-fluorospiro[indol-3,4'-piperidin]-1(2H)-yl}(2-chloropyridin-4-yl)methanone (known from WO2003/106457), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diazaspiro[4.5]dec-3-en-4-yl ethyl carbonate (known from WO2009/049851), 4-(but-2-yn-1-yloxy)-6-(3,5-dimethylpiperidin-1-yl)-5-fluoropyrimidine (known from WO2004/099160), (2,2,3,3,4,4,5,5-octafluoropentyl)(3,3,3-trifluoropropyl)malononitrile (known from WO2005/063094), (2,2,3,3,4,4,5,5-octafluoropentyl)(3,3,4,4,4-pentafluorobutyl)malononitrile (known from WO2005/063094), 8-[2-(cyclopropylmethoxy)-4-(trifluoromethyl)phenoxy]-3-[6-(trifluoromethyl)pyridazin-3-yl]-3-azabicyclo[3.2.1]octane (known from WO2007/040280), 2-ethyl-7-methoxy-3-methyl-6-[(2,2,3,3-tetrafluoro-2,3-dihydro-1,4-benzodioxin-6-yl)oxy]quinolin-4-yl methyl carbonate (known from JP2008/110953), 2-ethyl-7-methoxy-3-methyl-6-[(2,2,3,3-tetrafluoro-2,3-dihydro-1,4-benzodioxin-6-yl)oxy]quinolin-4-yl acetate (known from JP2008/110953), PF1364 (CAS-Reg. No. 1204776-60-2) (known from JP2010/018586), 5-[5-(3,5-dichlorophenyl)-5-(trifluoromethyl)-4,5-dihydro-1,2-oxazol-3-yl]-2-(1H-1,2,4-triazol-1-yl)benzonitrile (known from WO2007/075459), 5-[5-(2-chloropyridin-4-yl)-5-(trifluoromethyl)-4,5-dihydro-1,2-oxazol-3-yl]-2-(1H-1,2,4-triazol-1-yl)benzonitrile (known from WO2007/075459), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]ethyl}benzamide (known from WO2005/085216), 4-{[(6-chloropyridin-3-yl)methyl](cyclopropyl)amino}-1,3-oxazol-2(5H)-one, 4-{[(6-chloropyridin-3-yl)methyl](2,2-difluoroethyl)amino}-1,3-oxazol-2(5H)-one, 4-{[(6-chloropyridin-3-yl)methyl](ethyl)amino}-1,3-oxazol-2(5H)-one, 4-{[(6-chloropyridin-3-yl)methyl](methyl)amino}-1,3-oxazol-2(5H)-one (all known from WO2010/005692), NNI-0711 (known from WO2002096882), 1-acetyl-N-[4-(1,1,1,3,3,3-hexafluoro-2-methoxypropan-2-yl)-3-isobutylphenyl]-N-isobutyryl-3,5-dimethyl-1H-pyrazole-4-carboxamide (known from WO2002096882), methyl 2-[2-({[3-bromo-1-(3-chloropyridin-2-yl)-1H-pyrazol-5-yl]carbonyl}amino)-5-chloro-3-methylbenzoyl]-2-methylhydrazine carboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazine carboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazine carboxylate (known from WO2005/085216), methyl 2-[3,5-dibromo-2-({[3-bromo-1-(3-chloropyridin-2-yl)-1H-pyrazol-5-yl]carbonyl}amino)benzoyl]-1,2-diethylhydrazine carboxylate (known from WO2005/085216), methyl 2-[3,5-dibromo-2-({[3-bromo-1-(3-chloropyridin-2-yl)-1H-pyrazol-5-yl]carbonyl}amino)benzoyl]-2-ethylhydrazine carboxylate (known from WO2005/085216), (5RS,7RS;5RS,7SR)-1-(6-chloro-3-pyridylmethyl)-1,2,3,5,6,7-hexahydro-7-methyl-8-nitro-5-propoxyimidazo[1,2-a]pyridine (known from WO2007/101369), 2-{6-[2-(5-fluoropyridin-3-yl)-1,3-thiazol-5-yl]pyridin-2-yl}pyrimidine (known from WO2010/006713), 2-{6-[2-(pyridin-3-yl)-1,3-thiazol-5-yl]pyridin-2-yl}pyrimidine (known from WO2010/006713).

Fungicides:

(1) Ergosterol biosynthesis inhibitors, such as, for example, aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulphate, imibenconazole, ipconazole, metconazole, myclobutanil, haftifine, nuarimol, oxpoconazole, paclobutrazol, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, uniconazole, uniconazole-p, viniconazole, voriconazole, 1-(4-chlorophenyl)-2-(1H-1,2,4-triazol-1-yl) cycloheptanol, methyl 1-(2,2-dimethyl-2,3-dihydro-1H-inden-1-yl)-1H-imidazole 5-carboxylate, N'-{5-(difluoromethyl)-2-methyl-4-[3-(trimethylsilyl)propoxy]phenyl}-N-ethyl-N-methylimidoformamide, N-ethyl-N-methyl-N'-{2-methyl-5-(trifluoromethyl)-4-[3-(trimethylsilyl)propoxy]-phenyl}imidoformamide and O-[1-(4-methoxyphenoxy)-3,3-dimethylbutan-2-yl]-1H-imidazole-1-carbothioate.

(2) Respiration inhibitors (respiratory-chain inhibitors), such as, for example, bixafen, boscalid, carboxin, diflumetorim, fenfuram, fluopyram, flutolanil, flaxapyroxad, furametpyr, furmecyclox, isopyrazam mixture of the syn-epimeric racemate 1RS,4SR,9RS and of the anti-epimeric racemate 1RS,4SR,9SR, isopyrazam (anti-epimeric racemate), isopyrazam (anti-epimeric enantiomer 1R,4S,9S), isopyrazam (anti-epimeric enantiomer 1S,4R,9R), isopyrazam (syn-epimeric racemate 1RS,4SR,9RS), isopyrazam (syn-epimeric enantiomer 1R,4S,9R), isopyrazam (syn-epimeric enantiomer 1S,4R,9S), mepronil, oxycarboxin, penflufen, penthiopyrad, sedaxane, thifluzamid, 1-methyl-N-[2-(1,1,2,2-tetrafluoroethoxy)phenyl]-3-(trifluoromethyl)-1H-pyrazole-4-carboxamide, 3-(difluoromethyl)-1-methyl-N-[2-(1,1,2,2-tetrafluoroethoxy)phenyl]-1H-pyrazole-4-carboxamide, 3-(difluoromethyl)-N-[4-fluoro-2-(1,1,2,3,3,3-hexafluoropropoxy)phenyl]-1-methyl-1H-pyrazole-4-carboxamide and N-[1-(2,4-dichlorophenyl)-1-methoxypropan-2-yl]-3-(difluoromethyl)-1-methyl-1H-pyrazole-4-carboxamide.

(3) Respiration inhibitors (respiratory-chain inhibitors) on the complex III of the respiratory chain, such as, for example, ametoctradin, amisulbrom, azoxystrobin, cyazofamid, dimoxystrobin, enestroburin, famoxadon, fenamidon, fluoxastrobin, kresoxim-methyl, metominostrobin, orysastrobin, picoxystrobin, pyraclostrobin, pyrametostrobin, pyraoxystrobin, pyribencarb, trifloxystrobin, (2E)-2-(2-{[6-(3-chloro-2-methylphenoxy)-3-fluoropyrimidin-4-yl]oxy}phenyl)-2-(methoxyimino)-N-methylethanamide, (2E)-2-(methoxyimino)-N-methyl-2-(2-{[({(1E)-1-[3-(trifluoromethyl)phenyl]ethyliden}amino)oxy]methyl}phenyl)ethanamide, (2E)-2-(methoxyimino)-N-methyl-2-{2-[(E)-({1-[3-(trifluoromethyl)phenyl]ethoxy}imino)methyl]phenyl}-ethanamide, (2E)-2-{2-[({[(1E)-1-(3-{[(E)-1-fluoro-2-phenylethenyl]oxy}phenyl)ethyliden]-amino}oxy)methyl]phenyl}-2-(methoxyimino)-N-methylethanamide, (2E)-2-{2-[({[(2E,3E)-4-(2,6-dichlorophenyl)but-3-en-2-ylidene]amino}oxy)methyl]phenyl}-2-(methoxyimino)-N-methylethanamide, 2-chloro-N-(1,1,3-trimethyl-2,3-dihydro-1H-inden-4-yl)pyridine-3-carboxamide, 5-methoxy-2-methyl-4-(2-{[({(1E)-1-[3-(trifluoromethyl)phenyl]ethyliden}amino)oxy]methyl}-phenyl)-2,4-dihydro-3H-1,2,4-triazol-3-one, methyl (2E)-2-{2-[({cyclopropyl[(4-methoxyphenyl)imino]methyl} sulphanyl)methyl]phenyl}-3-methoxyprop-2-enoate, N-(3-ethyl-3,5,5-trimethylcyclohexyl)-3-(formylamino)-2-hydroxybenzamide, 2-{2-[(2,5-dimethylphenoxy)-methyl]phenyl}-2-methoxy-N-methylacetamide and (2R)-2-{2-[(2,5-dimethylphenoxy)methyl]-phenyl}-2-methoxy-N-methylacetamide.

(4) Mitosis and cell division inhibitors, such as, for example, benomyl, carbendazim, chlorfenazole, diethofencarb, ethaboxam, fluopicolid, fuberidazole, pencycuron, thiabendazole, thiophanate-methyl, thiophanate, zoxamide, 5-chloro-7-(4-methylpiperidin-1-yl)-6-(2,4,6-trifluorophenyl)[1,2,4]triazolo[1,5-a]pyrimidine and 3-chloro-5-(6-chloropyridin-3-yl)-6-methy-4-(2,4,6-trifluorophenyl)pyridazine.

(5) Compounds with multi-site activity, such as, for example, Bordeaux mixture, captafol, captan, chlorothalonil, copper preparations such as copper hydroxide, copper naphthenate, copper oxide, copper oxychloride, copper sulphate, dichlofluanid, dithianon, dodine, dodine free base, ferbam, fluorofolpet, folpet, guazatine, guazatine acetate, iminoctadine, iminoctadine albesilate, iminoctadine triacetate, man copper, mancozeb, maneb, metiram, metiram-zinc, oxine-copper, propamidine, propineb, sulphur and sulphur preparations such as, for example, calcium polysulphide, thiram, tolylfluanid, zineb and ziram.

(6) Resistance inductors, such as, for example, acibenzolar-5-methyl, isotianil, probenazole and tiadinil.

(7) Amino acid and protein biosynthesis inhibitors, such as, for example, andoprim, blasticidin-S, cyprodinil, kasugamycin, kasugamycin hydrochloride hydrate, mepanipyrim and pyrimethanil.

(8) ATP production inhibitors, such as, for example, fentin acetate, fentin chloride, fentin hydroxide and silthiofan.

(9) Cell wall synthesis inhibitors, such as, for example, benthiavalicarb, dimethomorph, flumorph, iprovalicarb, mandipropamid, polyoxins, polyoxorim, validamyein A and valifenalate.

(10) Lipid and membrane synthesis inhibitors, such as, for example, biphenyl, chloroneb, dicloran, edifenphos, etridiazole, iodocarb, iprobenfos, isoprothiolane, propamocarb, propamocarb hydrochloride, prothiocarb, pyrazophos, quintozene, tecnazene and tolclofos-methyl.

(11) Melanin biosynthesis inhibitors, such as, for example, carpropamid, diclocymet, fenoxanil, fthalide, pyroquilon and tricyclazole.

(12) Nucleic acid synthesis inhibitors, such as, for example, benalaxyl, benalaxyl M (kiralaxyl), bupirimate, clozylacon, dimethirimol, ethirimol, furalaxyl, hymexazol, metalaxyl, metalaxyl-M (mefenoxam), ofurace, oxadixyl and oxolinic acid.

(13) Signal transduction inhibitors, such as, for example, chlozolinate, fenpiclonil, fludioxonil, iprodione, procymidon, quinoxyfen and vinclozoline.

(14) Decouplers, such as, for example, binapacryl, dinocap, ferimzone, fluazinam and meptyldinocap.

(15) Further compounds, such as, for example, benthiazole, bethoxazin, capsimycin, carvone, chinomethionat, chlazafenon, cufraneb, cyflufenamid, cymoxanil, cyprosulfamide, dazomet, debacarb, dichlorophen, diclomezine, difenzoquat, difenzoquat methylsulphate, diphenylamine, ecomat, fenpyrazamine, flumetover, fluoromid, flusulfamide, flutianil, fosetyl-aluminium, fosetyl-calcium, fosetyl-sodium, hexachlorobenzene, irumamycin, methasulphocarb, methyl isothiocyanate, metrafenone, mildiomycin, natamycin, nickel dimethyldithiocarbamate, nitrothal-isopropyl, octhilinone, oxamocarb, oxyfenthiin, pentachlorophenol and its salts, phenothrin, phosphoric acid and its salts, propamocarb-fosetylate, propanosine-sodium, proquinazid, pyrrolnitrin, tebufloquin, tecloftalam, tolnifanid, triazoxide, trichlamide, zarilamide, 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{-4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-methoxyphenoxy)-3,3-dimethylbutan-2-yl 1H-imidazole-1-carboxylate, 2,3,5,6-tetrachloro-4-(methylsulphonyl)pyridine, 2,3-dibutyl-6-chlorothieno[2,3-d]pyrimidin-4(3H)-one, 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, 2-butoxy-6-iodo-3-propyl-4H-chromen-4-one, 2-chloro-5-[2-chloro-1-(2,6-difluoro-4-methoxyphenyl)-4-methyl-1H-imidazol-5-yl]pyridine, 2-phenylphenol and its salts, 3,4,5-trichloropyridine-2,6-dicarbonitrile, 3-[5-(4-chlorophenyl)-2,3-dimethyl-1,2-oxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 5-amino-1,3,4-thiadiazole-2-thiol, 5-enyl-N'-(prop-2-yn-1-yl)thiophene-2-sulphonohydrazide, 5-methyl-6-octyl[1,2,4]triazolo[1,5-a]pyrimidin-7-amine, ethyl (2Z)-3-amino-2-cyano-3-phenylprop-2-enoate, N-(4-chlorobenzyl)-3-[3-methoxy-4-(prop-2-yn-1-yloxy)phenyl] propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloropyridine-3-carboxamide, N-[1-(5-bromo-3-chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-{(E)-[(cyclopropylmethoxy)imino][6-(difluoromethoxy)-2,3-difluorophenyl]methyl}-2-phenylacetamide, N-{(Z)-[(cyclopropylmethoxy)imino][6-(difluoromethoxy)-2,3-difluorophenyl]methyl}-2-phenylacetamide, N-methyl-2-(1-[5-methyl-3-(trifluoromethyl)-1H-pyrazol-1-yl]acetyl piperidin-4-yl)-N-(1,2,3,4-tetrahydronaphthalen-1-yl)-1,3-thiazole-4-carboxamide, N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, pentyl {6-[({[(1-methyl-1H-tetrazol-5-yl)(phenyl)methylidene]amino}oxy)methyl]pyridin-2-yl}carbamate, phenazine-1-carboxylic acid, quinolin-8-ol and quinolin-8-ol sulphate (2:1).

(16) Further compounds, such as, for example, 1-methyl-3-(trifluoromethyl)-N-[2'-(trifluoromethyl)biphenyl-2-yl]-1H-pyrazole-4-carboxamide, N-(4'-chlorobiphenyl-2-yl)-3-(difluoromethyl)-1-methyl-1H-pyrazole-4-carboxamide, N-(2',4'-dichlorobiphenyl-2-yl)-3-(difluoromethyl)-1-methyl-1H-pyrazole-4-carboxamide, 3-(difluoromethyl)-1-methyl-N-[4'-(trifluoromethyl)biphenyl-2-yl]-1H-pyrazole-4-carboxamide, N-(2',5'-difluorobiphenyl-2-yl)-1-methyl-3-(trifluoromethyl)-1H-pyrazole-4-carboxamide, 3-(difluoromethyl)-1-methyl-N-[4'-(prop-1-yn-1-yl)biphenyl-2-yl]-1H-pyrazole-4-carboxamide, 5-fluoro-1,3-dimethyl-N-[4'-(prop-1-yn-1-yl)biphenyl-2-yl]-1H-pyrazole-4-carboxamide, 2-chloro-N-[4'-(prop-1-yn-1-yl)biphenyl-2-yl]pyridine-3-carboxamide, 3-(difluoromethyl)-N-[4'-(3,3-dimethylbut-1-yn-1-yl)biphenyl-2-yl]-1-methyl-1H-pyrazole-4-carboxamide, N-[4'-(3,3-dimethylbut-1-yn-1-yl)biphenyl-2-yl]-5-fluoro-1,3-dimethyl-1H-pyrazole-4-carboxamide, 3-(difluoromethyl)-N-(4'-ethynylbiphenyl-2-yl)-1-methyl-1H-pyrazole-4-carboxamide, N-(4'-ethynylbiphenyl-2-yl)-5-fluoro-1,3-dimethyl-1H-pyrazole-4-carboxamide, 2-chloro-N-(4'-ethynylbiphenyl-2-yl)pyridine-3-carboxamide, 2-chloro-N-[4'-(3,3-dimethylbut-1-yn-1-yl)biphenyl-2-yl]pyridine-3-carboxamide, 4-(difluoromethyl)-2-methyl-N-[4'-(trifluoromethyl)biphenyl-2-yl]-1,3-thiazole-5-carboxamide, 5-fluoro-N-[4'-(3-hydroxy-3-methylbut-1-yn-1-yl)biphenyl-2-yl]-1,3-dimethyl-1H-pyrazole-4-carboxamide, 2-chloro-N-[4'-(3-hydroxy-3-methylbut-1-yn-1-yl)biphenyl-2-yl]pyridine-3-carboxamide, 3-(difluoromethyl)-N-[4'-(3-methoxy-3-methylbut-1-yn-1-yl)biphenyl-2-yl]-1-methyl-1H-pyrazole-4-carboxamide, 5-fluoro-N-[4'-(3-methoxy-3-methylbut-1-yn-1-yl)biphenyl-2-yl]-1,3-dimethyl-1H-pyrazole-4-carboxamide, 2-chloro-N-[4'-(3-methoxy-3-methylbut-1-yn-1-yl)biphenyl-2-yl]pyridine-3-carboxamide, (5-bromo-2-methoxy-4-methylpyridin-3-yl)(2,3,4-trimethoxy-6-methylphenyl)methanone and N-[2-(4-{[3-(4-chlorophenyl)prop-2-yn-1-yl]oxy}-3-methoxyphenyl)ethyl]-N2-(methylsulphonyl)valinamide.

All of the stated co-components of classes (1) to (16) can form salts, where appropriate with suitable bases or acids, provided they are capable of so doing on the basis of their functional groups.

Each additional active compound may be mixed in a weight ratio of from 100:1 to 1:100, preferably from 5:1 to 1:5, with the active compounds according to the invention.

A mixture with other known active compounds, such as herbicides, fertilizers, growth regulators, safeners, semiochemicals, or else with agents for improving the plant properties, is also possible.

When used as insecticides, the active compounds according to the invention can furthermore be present in their commercially available formulations and in the use forms, prepared from these formulations, as a mixture with synergistic agents. Synergists are compounds which increase the action of the active compounds, without it being necessary for the synergist added to be active itself.

When used as insecticides, the active compounds according to the invention can furthermore be present in their commercially available formulations and in the use forms, prepared from these formulations, as a mixture with inhibitors which reduce degradation of the active compound after use in the environment of the plant, on the surface of parts of plants or in plant tissues.

The active compound content of the use forms prepared from the commercially available formulations can vary within wide limits. The active compound concentration of the use forms can be from 0.00000001 to 95% by weight of active compound, preferably between 0.00001 and 1% by weight.

The compounds are employed in a customary manner appropriate for the use forms.

All plants and plant parts can be treated in accordance with the invention. By plants are understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant varieties which can or cannot be protected by varietal property rights. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. The plant parts also include harvested material and also vegetative and generative propagation material, for example cuttings, tubers, rhizomes, slips and seed.

Treatment according to the invention of the plants and plant parts with the active compounds is carried out directly or by allowing the compounds to act on their surroundings, environment or storage space by the customary treatment methods, for example by immersion, spraying, evaporation, fogging, scattering, painting on, injection and, in the case of propagation material, in particular in the case of seeds, also by applying one or more coats.

As already mentioned above, it is possible to treat all plants and their parts according to the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering, if appropriate in combination with conventional methods (Genetically Modified Organisms), and parts thereof are treated. The terms "parts" or "parts of plants" or "plant parts" have been explained above.

Particularly preferably, plants of the plant cultivars which are in each case commercially available or in use are treated according to the invention. Plant cultivars are to be understood as meaning plants having new properties ("traits") and which have been obtained by conventional breeding, by mutagenesis or by recombinant DNA techniques. They can be cultivars, biotypes or genotypes.

Depending on the plant species or plant cultivars, their location and growth conditions (soils, climate, vegetation period, nutrition), the treatment according to the invention may also result in superadditive ("synergistic") effects. Thus possible are, for example, reduced application rates and/or a widening of the activity spectrum and/or an increase of the activity of the compounds and compositions usable according to the invention, better plant growth, increased tolerance to high or low temperatures, increased tolerance to drought or to water or soil salt content, increased flowering, easier harvesting, accelerated maturation, higher harvest yields, higher quality and/or higher nutritional value of the harvested products, increased storability and/or processability of the harvested products, which exceed the effects normally to be expected.

The preferred transgenic plants or plant cultivars (i.e. those obtained by genetic engineering) which are to be treated according to the invention include all plants which, in the genetic modification, received genetic material which imparts particular advantageous useful properties ("traits") to these plants. Examples of such properties are better plant growth, increased tolerance to high or low temperatures, increased tolerance to drought or to water or soil salt content, increased flowering, easier harvesting, accelerated maturation, higher harvest yields, higher quality and/or a higher nutritional value of the harvested products, better storability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other types of vegetable, cotton, tobacco, oilseed rape and also fruit plants (with the fruits apples, pears, citrus fruits and grapes), with particular emphasis being given to maize, soy beans, potatoes, cotton, tobacco and oilseed rape. Traits that are emphasized in particular are increased defence of the plants against insects, arachnids, nematodes and slugs and snails by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are also particularly emphasized are the increased defence of the plants against fungi, bacteria and viruses by systemic acquired resistance (SAR), systemin, phytoalexins, elicitors and also resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinothricin (for example the "PAT" gene). The genes which impart the desired traits in question can also be present in combinations with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soy bean varieties which are sold under the trade names Roundup Ready® (tolerance against glyphosate, for example maize, cotton, soy beans), Liberty Link® (tolerance against phosphinothricin, for example oilseed rape), IMI® (tolerance against imidazolinones) and STS®(tolerance against sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plants will be developed and/or marketed in the future.

The plants listed can be treated according to the invention in a particularly advantageous manner with the compounds of the formula (I) and/or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The active compounds according to the invention act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example *Pulex* spp., *Ctenocephalides* spp. (*Ctenocephalides canis*, *Ctenocephalides felis*), *Xenopsylla* spp., *Ceratophyllus* spp.

From the order of the Heteropterida, for example, *Cimex* spp., *Triatoma* spp., *Rhodnius* spp. and *Panstrongylus* spp.

From the order of the Blattarida, for example *Blatta orientalis*, *Periplaneta americana*, *Blattella germanica* and *Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., Hypodectes spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for livestock, poultry, domestic animals and the like, the active compounds of the formula (I) can be used as formulations (for example powders, emulsions, flowables) comprising the active compounds in an amount of from 1 to 80% by weight, either directly or after 100 to 10 000-fold dilution, or they may be used as a chemical bath.

It has furthermore been found that the compounds according to the invention have a strong insecticidal action against insects which destroy industrial materials.

The following insects may be mentioned as examples and as preferred—but without limitation:

beetles, such as *Hylotrupes bajulus*, *Chlorophorus pilosis*, *Anobiurr punctatum*, *Xestobium rufovillosum*, *Ptilinus pecticornis*, *Dendrobium pertinex*, *Ernobius mollis*, *Priobium carpini*, *Lyctus brunneus*, *Lyctus africanus*, *Lyctus planicollis*, *Lyctus linearis*, *Lyctus pubescens*, *Trogoxylon aequale*, *Minthes rugicollis*, *Xyleborus* spec. *Tryptodendron* spec. *Apate monachus*, *Bostrychus capucins*, *Heterobostrychus brunneus*, *Sinoxylon* spec. *Dinoderus minutus*;

Hymenoptera, such as *Sirex juvencus*, *Urocerus gigas*, *Urocerus gigas taignus*, *Urocerus augur*;

termites, such as *Kalotermes flavicollis*, *Cryptotermes brevis*, *Heterotermes indicola*, *Reticulitermes flavipes*, *Reticulitermes santonensis*, *Reticulitermes lucifugus*, *Mastotermes darwiniensis*, *Zootermopsis nevadensis*, *Coptotermes formosanus*;

bristletails, such as *Lepisma saccarina*.

Industrial materials in the present connection are to be understood as meaning non-living materials, such as, preferably, plastics, adhesives, sizes, papers and cards, leather, wood and processed wood products and coating compositions.

The ready-to-use compositions can also comprise other insecticides, if appropriate, and also one or more fungicides, if appropriate.

With respect to possible additional partners for mixing, reference is made to the insecticides and fungicides mentioned above.

The compounds according to the invention can at the same time be employed for protecting objects which come into contact with saltwater or brackish water, such as hulls, screens, nets, buildings, moorings and signalling systems in particular, against fouling.

Furthermore, the compounds according to the invention can be used alone or in combinations with other active compounds as antifouling compositions.

The active compounds are also suitable for controlling animal pests in the domestic field, in hygiene and in the protection of stored products, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus*.

From the order of the Acarina, for example, *Argas persicus*, *Argas reflexus*, *Bryobia* spp., *Dermanyssus gallinae*, *Glyciphagus domesticus*, *Ornithodorus moubat*, *Rhipicephalus sanguineus*, *Trombicula alfreddugesi*, *Neutrombicula autumnalis*, *Dermatophagoides pteronissimus*, *Dermatophagoides forinae*.

From the order of the Araneae, for example, Aviculariidae, Araneidae.

From the order of the Opiliones, for example, *Pseudoscorpiones chelifer*, *Pseudoscorpiones cheiridium*, *Opiliones phalangium*.

From the order of the Isopoda, for example, *Oniscus asellus*, *Porcellio scaber*.

From the order of the Diplopoda, for example, *Blaniulus guttulatus, Polydesmus* spp.

From the order of the Chilopoda, for example, *Geophilus* spp.

From the order of the Zygentoma for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Pemphigus* spp., *Phylloera vastatrix, Phthirus pubis.*

From the order of the Heteroptera, for example, *Cimex hemipterus, Cimex lectularius, Rhodinus prolixus, Triatoma infestans.*

In the field of household insecticides, they are used alone or in combination with other suitable active compounds, such as phosphoric acid esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or in bait stations.

PREPARATION EXAMPLES

Example 1

2-[6-(4-Fluoro-2-pyridin-3-ylthiazol-5-yl)pyridin-2-yl]pyrimidine

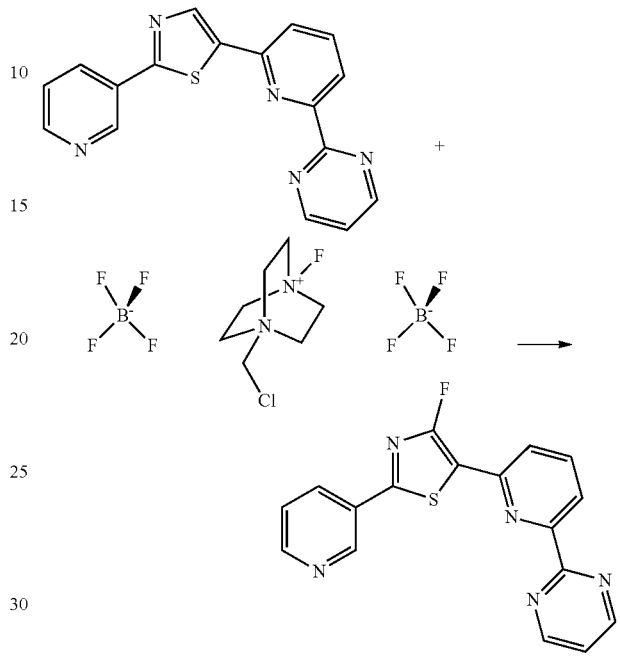

0.5 g (1.57 mmol) of 2-[6-(2-pyridin-3-ylthiazol-5-yl)pyridin-2-yl]pyrimidine was dissolved in acetonitrile, 1.16 g (3.15 mmol) of 1-(chloromethyl)-4-fluoro-1,4-diazoniabicyclo[2.2.2]octane ditetrafluoroborate (Selectfluor™) and 1 g (7.04 mmol) of sodium sulphate were added and the mixture was heated at reflux overnight and, after cooling, filtered through Celite. The filtrate was concentrated and purified by chromatography (cyclohexane/ethyl acetate, then ethyl acetate/methanol).

Yield: 62.0 mg (11% of theory)

HPLC-MS: log P(HCOOH)=2.15; mass (m/z): 336.1 (M+H)$^+$; $^1$H-NMR (D6-DMSO): 7.60 (m, 2H), 8.00 (d, 1H), 8.15 (t, 1H), 8.35 (d, 1H), 8.40 (d, 1H), 8.75 (d, 1H), 9.05 (m, 2H), 9.20 ppm (m, 1H).

Example 2

2-{6-[4-Chloro-2-(pyridin-3-yl)-1,3-thiazol-5-yl]pyridin-2-yl}pyrimidine and 5-chloro-2-{6-[4-chloro-2-(pyridin-3-yl)-1,3-thiazol-5-yl]pyridin-2-yl}pyrimidine

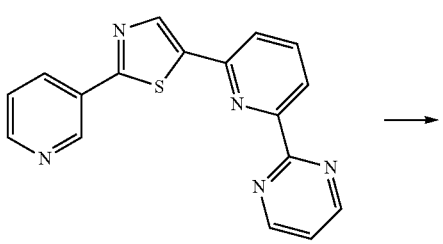

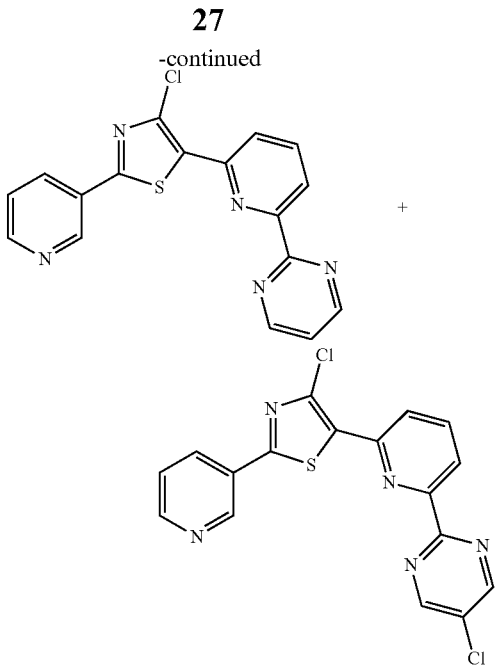

325 mg (993 μmol) of 2-[6-(2-pyridin-3-ylthiazol-5-yl) pyridin-2-yl]pyrimidine were dissolved in 6 ml of dimethylformamide, 146 mg (1.09 mmol) of N-chlorosuccinimide were added and the mixture was heated at 80° C. for 6 hours. More N-chlorosuccinimide (1 eq.) was added, and the mixture was then stirred at 80° C. for a further 14 hours. The reaction mixture was added to water and extracted repeatedly with ethyl acetate. The combined organic phases were dried over magnesium sulphate, filtered and concentrated. The crude product was purified chromatographically (cyclohexane/ethyl acetate).

2-{6-[4-Chloro-2-(pyridin-3-yl)-1,3-thiazol-5-yl]pyridin-2-yl}pyrimidine

Yield: 52.2 mg (15% of theory)
HPLC-MS: log P(HCOOH)=2.27; mass (m/z): 352.0 (M+H)+; 1H-NMR (D6-DMSO): 7.38 (t, 1H), 7.42 (m, 1H), 8.02 (t, 1H), 8.31 (m, 1H), 8.41 (d, 1H), 8.47 (d, 1H), 8.70 (m, 1H), 8.97 (d, 2H), 9.24 ppm (m, 1H).

5-Chloro-2-{6-[4-chloro-2-(pyridin-3-yl)-1,3-thiazol-5-yl]pyridin-2-yl}pyrimidine Yield: 15 mg (4% of theory)
HPLC-MS: log P(HCOOH)=3.27; mass (m/z): 385.9; 387.9 (M+H)+; 1H-NMR (D6-DMSO): 7.44 (m, 1H), 8.02 (t, 1H), 8.33 (m, 1H), 8.41 (d, 1H), 8.43 (d, 1H), 8.71 (m, 1H), 8.91 (s, 2H), 9.24 ppm (m, 1H).

1) Description of the Method for Determining the logP Values (Formic Acid Method)

The logP values were determined in accordance with EEC Directive 79/831 Annex V.A8 by HPLC (High Performance Liquid Chromatography) using a reversed-phase column (C 18). Temperature: 55° C.

Mobile phases for determination in the acidic range (pH 3.4):
Mobile phase A: acetonitrile+1 ml of formic acid/litre.
Mobile phase B: water+0.9 ml of formic acid/litre.
Gradient: 10% mobile phase A/90% mobile phase B to 95% mobile phase A/5% mobile phase B over 4.25 min.

Calibration was carried out using unbranched alkan-2-ones (having from 3 to 16 carbon atoms) with known logP values (the logP values were determined by the retention times using linear interpolation between two successive alkanones). The lambda max values were determined in the maxima of the chromatographic signals using the UV spectra from 200 nm to 400 nm.

BIOLOGICAL EXAMPLES

Myzus Test

Spray Treatment

Solvent: 78 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration. Discs of Chinese cabbage (*Brassica pekinensis*) infected by all stages of the green peach aphid (*Myzus persicae*) are sprayed with an active compound preparation of the desired concentration.

After 6 days, the effect in % is determined. 100% means that all of the aphids have been killed; 0% means that none of the aphids have been killed.

In this test, for example, the following compounds of the Preparation Examples show, at an application rate of 500 g/ha, an effect of 100%:
Ex. No. 1

The invention claimed is:
1. A compound of formula (I)

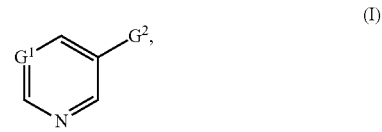

or a salt or N-oxide thereof,
in which
G$^1$ represents CH or C-halogen,
G$^2$ represents

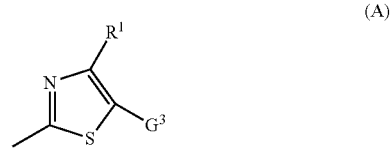

in which
R$^1$ represents cyano, nitro, or halogen, and
G$^3$ represents a substituted heterocycle selected from the group consisting of dioxanyl, oxazolinyl, dihydrooxadiazinyl, dihydrodioxazinyl, and hydroxypyridyl; or heteroaryl which is substituted by an optionally substituted heterocyclyl selected from the group consisting of triazolinonyl, dihydrodioxazinyl, dihydrooxadiazinyl, dioxolanyl, dioxanyl, piperidinonyl, pyrrolidinonyl, and pyrazolinonyl; by an optionally substituted phenyl; by an optionally substituted heteroaryl; or by an optionally substituted heteroarylalkyl.

2. The compound according to claim 1, in which $G^3$ represents a substituted heterocycle.

3. The compound according to claim 1, in which $G^3$ represents substituted heteroaryl.

4. A method for controlling pests, comprising applying at least one compound according to claim 1 to a plant, a plant part, surroundings of a plant, environment of a plant, storage space of a plant, or a combination thereof.

5. A composition comprising at least one compound according to claim 1 and auxiliaries, solvents, carriers, surfactants, extenders, or combinations thereof.

6. The compound of claim 1, wherein $G^3$ is 1,3-dioxan-2-yl.

7. The compound of claim 1, wherein $G^3$ is 2-pyrimidinyl.

8. The compound of claim 1, wherein $R^1$ is fluorine or chlorine.

9. The compound of claim 1, wherein $G^1$ is CH.

10. The compound of claim 1, wherein the compound is selected from the group consisting of:
2-[6-(4-Fluoro-2-pyridin-3-ylthiazol-5-yl)pyridin-2-yl]pyrimidine;
2-{6-[4-Chloro-2-(pyridin-3-yl)-1,3-thiazol-5-yl]pyridin-2-yl}pyrimidine; and
5-Chloro-2-{6-[4-chloro-2-(pyridin-3-yl)-1,3-thiazol-5-yl]pyridin-2-yl}pyrimidine.

11. The compound of claim 1, wherein $G^3$ is a heterocycle selected from the group consisting of 1,3-dioxan-2-yl, oxazolinyl, dihydrooxadiazinyl, dihydrodioxazinyl, and hydroxypyridyl, any of which is substituted by one or more halogen, cyano, nitro, $C_1$-$C_6$-alkyl, $C_1$-$C_6$-haloalkyl, $C_3$-$C_6$-cycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-alkylsulphonyl, $C_1$-$C_6$-haloalkylsulphinyl, $C_1$-$C_6$-haloalkylsulphonyl, amino, $C_1$-$C_6$-alkylamino, di-($C_1$-$C_6$-alkyl)amino, $C_1$-$C_6$-alkylcarbonylamino, $C_1$-$C_6$-alkoxycarbonylamino, $C_1$-$C_6$-alkoxy-$C_1$-$C_6$-alkyl, $C_1$-$C_6$-haloalkoxy-$C_1$-$C_6$-alkyl, $C_2$-$C_6$-alkenyl, $C_2$-$C_6$-alkynyl, $C_3$-$C_6$-cycloalkyl-$C_1$-$C_6$-alkyl, $C_1$-$C_6$-alkylcarbonyl, $C_1$-$C_6$-alkoxycarbonyl, aminocarbonyl, pyridyl, or pyrimidyl; or
is a heteroaryl selected from the group consisting of pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl, and indolizinyl, any of which is substituted
by a heterocyclyl selected from the group consisting of triazolinonyl, dihydrodioxazinyl, dihydrooxadiazinyl, dioxolanyl, dioxanyl, piperidinonyl, pyrrolidinonyl, and pyrazolinonyl, any of which may be substituted by $C_1$-$C_6$-alkyl or $C_1$-$C_6$-haloalkyl;
by phenyl, which may be substituted by halogen, cyano, nitro, $C_1$-$C_6$-alkyl, or $C_1$-$C_6$-haloalkyl;
by a heteroaryl selected from the group consisting of pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl, and isoquinolinyl, any of which may be substituted by halogen, nitro, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxy-$C_1$-$C_6$alkyl, $C_1$-$C_6$alkylthio-$C_1$-$C_6$-alkyl, or $C_3$-$C_6$-cycloalkyl; or
by a heteroarylalkyl selected from the group consisting of triazolyl-$C_1$-$C_6$-alkyl, pyridyl-$C_1$-$C_6$-alkyl, pyrimidyl-$C_1$-$C_6$-alkyl, and oxadiazolyl-$C_1$-$C_6$-alkyl, any of which may be substituted by $C_1$-$C_6$-alkyl.

12. The compound of claim 1, wherein $G^3$ is a heterocycle selected from the group consisting of 1,3-dioxan-2-yl, oxazolinyl, dihydrooxadiazinyl, dihydrodioxazinyl and hydroxypyridyl, any of which is substituted by one or more halogen, cyano, nitro, $C_1$-$C_6$-alkyl, $C_1$-$C_6$-haloalkyl, $C_3$-$C_6$-cycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-alkylsulphonyl, $C_1$-$C_6$-haloalkylsulphinyl, $C_1$-$C_6$-haloalkylsulphonyl, amino, $C_1$-$C_6$-alkylamino, di-($C_1$-$C_6$-alkyl)amino, $C_1$-$C_6$-alkylcarbonylamino, $C_1$-$C_6$-alkoxycarbonylamino, $C_1$-$C_6$-alkoxy-$C_1$-$C_6$-alkyl, $C_1$-$C_6$-haloalkoxy-$C_1$-$C_6$-alkyl, $C_2$-$C_6$-alkenyl, $C_2$-$C_6$-alkynyl, $C_3$-$C_6$-cycloalkyl-$C_1$-$C_6$alkyl, $C_1$-$C_6$-alkylcarbonyl, $C_1$-$C_6$-alkoxycarbonyl, aminocarbonyl, pyridyl, or pyrimidyl; or
is a heteroaryl selected from the group consisting of pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl, and indolizinyl, any of which is substituted by a heterocyclyl selected from the group consisting of triazolinonyl, dihydrodioxazinyl, dihydrooxadiazinyl, dioxolanyl, dioxanyl, piperidinonyl, pyrrolidinonyl, and pyrazolinonyl;
by phenyl, which may be substituted by halogen, cyano, nitro, $C_1$-$C_6$-alkyl, or $C_1$-$C_6$-haloalkyl;
by a heteroaryl selected from the group consisting of pyrrolyl, pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl, and isoquinolinyl, any of which may be substituted by halogen, nitro, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, $C_1$-$C_6$-alkylthio-$C_1$-$C_6$-alkyl, or $C_3$-$C_6$-cycloalkyl; or
by a heteroarylalkyl selected from the group consisting of triazolyl-$C_1$-$C_6$-alkyl, pyridyl-$C_1$-$C_6$-alkyl, pyrimidyl-$C_1$-$C_6$-alkyl, and oxadiazolyl-$C_1$-$C_6$-alkyl, any of which may be substituted by $C_1$-$C_6$-alkyl.

13. The compound of claim 1, wherein $G^3$ is selected from the group consisting of optionally pyridyl- or pyrimidinyl-substituted 1,3-dioxan-2-yl, oxazolinyl, dihydrooxadiazinyl, and hydroxypyridyl; or
is selected from the group consisting of pyrazolyl, 1,2,4-oxadiazolyl, pyridyl, pyrimidinyl, 1,3,5-triazinyl, triazinyl, and oxadiazolyl, any of which is substituted
by a heterocyclyl selected from the group consisting of triazolinonyl, dihydrodioxazinyl, dihydrooxadiazinyl, piperidinonyl, pyrrolidinonyl, and pyrazolinonyl, any of which may be substituted by $C_1$-$C_4$-alkyl or $C_1$-$C_4$-haloalkyl;

by phenyl, which may be substituted by halogen;

by a heteroaryl selected from the group consisting of pyrrolyl, pyridyl, pyridyl N-oxide, pyrimidinyt, pyrazolyl, thiazolyl, furanyl, thienyl, triazolyl, oxadiazolyl, thiadiazelyl, pyrazinyl, triazinyl, and isoquinolinyi, any of which may be substituted by halogen, nitro, $C_1$-$C_4$-alkyl, $C_1C_1$haloalkyl, $C_1$-$C_4$-alkoxy, or $C_3$-$C_6$-cycloatkyl; or by a heteroarylalkyl selected from the group consisting of triazolyl-$C_1$-$C_4$-alkyl, pyridyl-$C_1$-$C_4$-alkyl, pyrimidinyl-$C_1$-$C_4$-alkyl, and oxadiazolyl-$C_1$-$C_4$-alkyl, any of which may be substituted by $C_1$-$C_4$-alkyl.

* * * * *